United States Patent [19]

Brunelle et al.

[11] Patent Number: 5,100,804
[45] Date of Patent: Mar. 31, 1992

[54] METHOD FOR DETERMINING CHLOROFORMATE CONCENTRATION

[75] Inventors: Daniel J. Brunelle, Scotia; David K. Bonauto, Newburgh; Eugene P. Boden, Scotia, all of N.Y.

[73] Assignee: General Electric Company, Schenectady, N.Y.

[21] Appl. No.: 669,161

[22] Filed: Mar. 14, 1991

[51] Int. Cl.$^5$ ............................................. C01N 27/10
[52] U.S. Cl. ................................... 436/126; 436/124; 436/163; 528/370; 528/371
[58] Field of Search ............................. 436/124–126, 436/163; 528/370–373

[56] References Cited

U.S. PATENT DOCUMENTS 4,644,053 2/1987 Brunelle .............................. 528/371
4,727,134 2/1988 Brunelle .............................. 528/371

*Primary Examiner*—David L. Lacey
*Assistant Examiner*—David Redding
*Attorney, Agent, or Firm*—William H. Pittman; James C. Davis, Jr.

[57] ABSTRACT

The molar concentration of chloroformate in an organic chloroformate solution is determined by adding an excess of a monohydroxyaromatic compound, water and a catalytic amount of a 4-dialkylaminopyridine such as 4-dimethylaminopyridine, titrating with aqueous base and taking as the end point the volume of base which achieves complete conversation of chloroformate groups to monoaromatic carbonate groups, as shown by a rapid rise in the pH of the aqueous phase of more than two points to a value in the range of 7–9. This method is particularly applicable to the determination of bischloroformate molar concentration in systems to be converted to cyclic polycarbonate oligomers. Conversion may be effected by condensation in the presence of a trialkylamine and aqueous base in the amount of about 3 moles per mole of bischloroformate.

17 Claims, No Drawings

METHOD FOR DETERMINING CHLOROFORMATE CONCENTRATION

This invention relates to the chemistry of chloroformates, and more particularly to the determination of chloroformate concentration in an organic solution.

Organic chloroformates are typically prepared by phosgenation of a hydroxyaromatic compound, typically in a mixed aqueous-organic medium and under alkaline conditions. The reaction mixture also frequently contains a catalytic amount of a trialkylamine.

Particularly useful chloroformates are the aromatic bischloroformates, both monomeric and oligomeric, prepared from dihydroxyaromatic compounds such as hydroquinone and 2,2-bis(4-hydroxyphenyl)propane, hereinafter sometimes designated "bisphenol A". Bischloroformates can be converted to linear polycarbonates, typically under alkaline conditions in the aforementioned mixed aqueous-organic media and in the presence of an interfacial polycarbonate formation catalyst such as a trialkylamine, the latter being present in larger amounts than those employed during bischloroformate preparation. They may also be converted to cyclic polycarbonate oligomers, useful intermediates for linear polycarbonates, under conditions similar to those employed for linear polycarbonate formation except that the bisphenol is maintained under high dilution conditions the equivalent thereof. Methods for the preparation of cyclic polycarbonate oligmers are disclosed, for example, in U.S. Pat. Nos. 4,644,053 and 4,727,134. Also of interest, by erason of their conversion to solvent-resistant polycarbonates, are the hydroquione-bisphenol cyclic copolycarbonate oligomers disclosed in U.S. Pat. No. 4,920, 200. All of the above-identified patents are incorporated by reference herein.

Various problems have been encountered in the preparation of cyclic polycarbonate oligomers on a large scale, as a result of misjudging the amount of base to be employed. While cyclics can often be prepared in good yield on a laboratory scale at a pH of the aqueous phase on the order of 13-14, they frequently undergo excessive hydrolysis at that level in larger scale reactions. pH levels on the order of 10-10.5 are frequently preferred. However, establishment of an optimum base level is complicated by difficulties in measuring the pH of a mixture comprising only a small proportion of water in combination with a large amount of organic liquid.

These problems are exacerbated in systems which include hydroquinone and its chloroformates. Such systems are particularly sensitive to base level, being even more subject to hydrolysis at high pH than systems involving only bisphenols such as bisphenol A. This may be due to the relatively high solubility of hydroquinone in water. At low pH, on the other hand, hydroquinone systems have a propensity to form relatively high molecular weight oligomers which are insoluble in organic liquids and are therefore lost during product isolation.

To avoid these problems, it would be highly beneficial to know the proportion or concentration of chloroformate groups in the organic phase of a reaction mixture. Such knowledge would permit precise establishment of an optimum base level. For example, conversion of bischloroformate to cyclic polycarbonate oligomers requires three equivalents of base per mole of bischloroformate: one equivalent for hydrolysis of a single chloroformate end group on each molecule, a second for cyclization with evolution of one mole of carbon dioxide, and a third for conversion of the evolved carbon dioxide to sodium bicarbonate. The overall reaction is as follows:

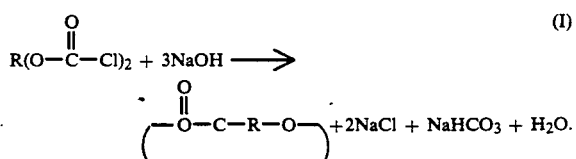

Nevertheless, a convenient method for the determination of chloroformate concentration in an organic solution has not previously been available. Instead, it has been necessary to convert a sample of the bischloroformate solution to monomeric/oligomeric phenyl carbonates by reaction with excess phenol in the presence of triethylamine, and then to analyze the proportions of the phenyl carbonate species therein by methods such as high pressure liquid chromatography.

Since this method does not determine the molar chloroformate concentration, it has been further necessary in the case of each chloroformate solution to conduct numerous small-scale conversions to cyclic oligomers, using different base concentrations, in order to determine the optimum concentration for the mixture being analyzed. It is by this burdensome and time-consuming sequence of operations that the optimum base levels disclosed in the aforementioned patents were determined.

The present invention is based on the discovery of a direct titration method for determination of the molar concentration of chloroformates in an organic solution. It is necessary to employ this method only once for each reaction mixture, and the result is a specific and accurate molar concentration. It is then possible to calculate the precise amount of base to be employed for conversion to cyclic polycarbonate oligomers, conversion to linear polycarbonates or other purposes.

In one of its aspects, therefore, the invention is a method for determining the chloroformate concentration of a solution of at least one organic chloroformate in a substantially non-polar organic liquid which comprises the steps of combining said solution with at least one monohydroxyaromatic compound in stoichiometric excess with respect to chloroformate; water, in the amount of about 5-25% by volume of said solution; and at least one 4-dialkylaminopyridine in the amount of about 1-10 mole percent based on the estimated amount of chloroformate; titrating said solution with aqueous base of known concentration under conditions facilitating reaction of chloroformate groups with the monohydroxyaromatic compound, and taking as the end point of the titration the volume of base which achieves complete conversion of chloroformate groups to monoaromatic carbonate groups as shown by a rapid rise in the pH of the aqueous phase of more than 2 points, to a value in the range of 7-11.

The method of this invention may be employed with any organic chloroformate or mixture of chloroformates. It is particularly useful for bischloroformates and especially aromatic bischloroformates, both monomeric and oligomeric. Typical monomeric bischloroformates are those represented by the relevant formula in equation I. They may be considered as derived from at least one dihydroxyaromatic compound of the formula HO—R—OH, wherein R is a divalent aromatic radical; oligomeric bischloroformates have a similar molecular structure with multiple R groups separated by carbonate groups.

The R values in the bischloroformates to which the invention is applicable may be different but are usually the same, and may be aliphatic, alicyclic, aromatic or mixed; those which are aliphatic or alicyclic generally contain up to about 8 carbon atoms. Suitable R values include ethylene, propylene, trimethylene, tetramethylene, hexamethylene, dodecamethylene, 1,4-(2-butenylene), 1,10-(2-ethyldecylene), 1,3-cyclopentylene, 1,3-cyclohexylene, 1,4-cyclohexylene, m-phenylene, p-phenylene, 4,4'-biphenylene, 2,2-bis(4-phenylene)propane, benzene-1,4-dimethylene (which is a vinylog of the ethylene radical and has similar properties) and similar radicals such as those which correspond to the dihydroxy compounds pounds disclosed by name or formula (generic or specific) in U.S. Pat. No. 4,217,438, the disclosure of which is incorporated by reference herein. Also included are radicals containing non-hydrocarbon moieties. These may be substituents such as chloro, nitro, alkoxy and the like, and also linking radicals such as thio, sulfoxy, sulfone, ester, amide, ether and carbonyl. Most often, however, all R radicals are hydocarbon radicals.

Preferably at least about 80% of the total number of R values, and most desirably all of said R values, are aromatic. The aromatic R radicals preferably have the formula (II) 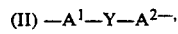

wherein each of $A^1$ and $A^2$ is a monocyclic divalent aromatic radical and Y is a bridging radical in which one or two atoms separate $A^1$ from $A^2$. The free valence bonds in formula II are usually in the meta or para positions of $A^1$ and $A^2$ in relation to Y.

In formula II, the $A^1$ and $A^2$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone.

For reasons of availability and particular suitability for the purposes of this invention, the preferred R radicals are p-phenylene and bis(4-phenylene)propane. The latter is derived from bisphenol A, and Y is isopropylidene and $A^1$ and $A^2$ are each p-phenylene therein.

The liquids employed in the method of this invention include those known to be useful in the preparation of linear and cyclic polycarbonates under interfacial reaction conditions. They are, for the most part, substantially non-polar organic liquids which form two-phase systems with water. Illustrative liquids of this type are aromatic hydrocarbons such as toluene and xylene; substituted aromatic hydrocarbons such as chlorobenzene, o-dichlorobenzene and nitrobenzene; and chlorinated aliphatic hydrocarbons such as chloroform and methylene chloride. The chlorinated aliphatic hydrocarbons are generally preferred, with methylene chloride being most preferred.

In the first step of the method of this invention, the chloroformate solution is combined with a number of materials including at least one monohydroxyaromatic compound. Suitable monohydroxyaromatic compounds include those which are useful for endcapping aromatic polycarbonates; they include phenol, p-cumylphenol and p-t-butylphenol. Phenol is generally preferred because of its availability and relatively low cost.

Also present are water and at least one 4-dialkylaminopyridine, the latter serving as a catalyst for the reaction between the chloroformate and the monohydroxyaromatic compound. The 4-dialkylaminopyridenes are employed for two reasons: first, the reaction between the chloroformate and the monohydroxyaromatic compound proceeds rapidly in their presence, and second, they are among the few amines that do not undergo a side reaction with chloroformates to form urethanes. The alkyl groups attached to the amine radical are most often primary or secondary $C_{1-4}$ alkyl groups and especially methyl. The pyridine ring is generally unsubstituted, although it may contain substituents such as chloro, nitro, acyl, alkyl or alkoxy. The preferred catalyst is 4-dimethylaminopyridene, again principally for reasons of operability and cost.

The amount of monohydroxyaromatic compound employed is a stoichiometric excess with respect to chloroformate; i.e., the ratio of equivalents of monohydroxyaromatic compound to chloroformate should be greater than 1:1, to ensure complete conversion of the chloroformate groups to aryl carbonate groups. Absent precise analytical details on the chloroformate, of the type provided by the above-described sequence of conversion to aryl carbonates and analysis by high pressure liquid chromatography, the required amount of monohydroxyaromatic compound must be estimated. Such estimates can readily be made by those skilled in the art. A considerable excess (e.g., an estimated ratio of equivalents of monohydroxyaromatic compound to chloroformate of about 2:1) is usually employed to insure the presence of an amount greater than stoichiometric.

The proportion of water employed is about 5-25% and preferably about 5-15% by volume, based on the organic solution. The proportion of 4-dialkylaminopyridene is about 1-10 mole percent, again based on the estimated amount of chloroformate in the solution.

It is frequently advantageous to include in the reaction mixture for the first step an additional portion of organic liquid, to produce a chloroformate solution more dilute than that in the reaction mixture being analyzed. The amount of organic liquid to be added is typically calculated to provide an estimated chloroformate concentration in the range of about 0.1-0.5M.

The combination produced in the first step of the method of this invention is subsequently titrated with aqueous base of known concentration, typically about 0.1-1.0M. Suitable aqueous bases include the alkali metal hydroxides, especially sodium hydroxide and potassium hydroxide. Its availability and low cost make sodium hydroxide the preferred base in most circumstances.

The conditions of the titration are those which will facilitate reaction of the chloroformate groups with the monohydroxyaromatic compound. Said reaction is normally quite rapid under alkaline conditions, and will take place spontaneously at temperatures in the range of about 0°–50° C. as base is added. When a relatively volatile organic liquid such as methylene chloride is employed, temperatures in the range of about 10°–30° C. are preferred with room temperature being particularly preferred.

Base is consumed as it is added in the titration reaction, to a total of one equivalent per equivalent of chloroformate groups. The products are the monoaromatic carbonate corresponding to the chloroformate, sodium chloride and water.

When conversion of chloroformate groups to monoaromatic carbonate groups is complete, further base addition causes a rapid rise in the pH of the aqueous phase of the titration mixture. The end point is taken to be the point at which a rise of more than 2 pH units takes place, to a final value in the range of 7-11. The pH of the aqueous phase can be conveniently monitored by the use of conventional electrometric titration means, or by the use of an indicator which is active in the crucial pH range. Illustrative indicators of this type are cresol red, thymol blue, metacresol purple, curcumin, metacresol purple and 4,4'-bis(4-amino-1-naphthylazo)-2,2'-stilbenedisulfonic acid.

As previously mentioned, the method of this invention is of particular use in the conversion of aromatic bischloroformates to the corresponding cyclic polycarbonate oligomers. Its accuracy permits the setting of a precise molar ratio of base to bischloroformate of 3:1. For this purpose, it is assumed that bischloroformate species are the only species in the reaction mixture, an assumption which is very close to the truth when the bischloroformate composition is produced by methods known in the art.

Accordingly, another aspect of the present invention is a method for preparing a cyclic polycarbonate composition which comprises the steps of titrating, as described hereinabove, a first portion of a solution of at least one aromatic bischloroformate in an organic liquid, to determine the chloroformate concentration of said solution; and effecting conversion of a second portion of bischloroformate to cyclic polycarbonate oligomers by condensation in the presence of a catalytic amount of at least one oleophilic aliphatic or alicyclic tertiary amine and about 3 moles of aqueous base per mole of bischloroformate.

In all respects other than the proportion of base, the method of this invention for preparing cyclic polycarbonate oligomers is the same as the method disclosed in the aforementioned U.S. Pat. Nos. 4,644,053, 4,727,134 and 4,920,200. The conditions of said method include maintenance of reagents in contact under conditions whereby the bischloroformate is present in low concentration (i.e., actual or simulated high dilution conditions, the latter being exemplified by gradual addition of bischloroformate to a reaction vessel containing solvent); maintenance of the temperature in the range of about 0°–50° C., most often about 0°–40° C. and preferably 20°–40° C.; employment of amine (preferably triethylamine) in a molar ratio to bischloroformate in the range of about 0.1-1.0:1 in the case of bisphenol bischloroformates, and in the range of about 0.06-2.0:1 and preferably about 0.1-0.25:1 in the case of reaction mixtures containing hydroquinone bischloroformates; and, preferably in many instances, maintenance of the amine concentration as constant as possible, typically by introduction in one initial large portion followed by incremental or continuous addition of the balance thereof. Reference is made to said patents for a detailed description of this method of preparation.

The invention is illustrated by the following examples.

EXAMPLE 1

A 100-ml. 3-necked flask was charged with 750 mg. (8 mmol.) of phenol, 5 mg. (0.04 mmol.) of 4-dimethylaminopyridine, 15 ml. of methylene chloride and 2 ml. of water. The mixture was stirred magnetically at a rate to ensure good mixing and there was added a 5.00-ml. portion (as measured by quantitative pipet) of a solution of bischloroformates of bisphenol A and hydroquinone in a molar ratio of 55:45, said solution having an estimated bischloroformate concentration of 0.7M. The pH of the mixture (which could be determined by reason of the aqueous phase thereof) was monitored with a pH probe which had been freshly calibrated at pH values of 7 and 10, and stirring was continued as the mixture was titrated with 0.500M aqueous sodium hydroxide solution. The pH remained fairly constant until at the end point it rose two or more pH units with the addition of 0.25-0.5 ml. of base. The chloroformate concentration was determined to be 0.7M.

A 500-ml. Morton flask equipped with a mechanical stirrer and condenser was charged with 100 ml. of methylene chloride, 5 ml. of water and 1.2 ml. (8.65 mmol.) of triethylamine. The mixture was heated to reflux with vigorous stirring and 100 ml. of the bischloroformate solution was pumped in (using a peristaltic pump) over 30 minutes, under the surface of the mixture in the flask. There was concurrently added 10.7 ml. (105 moles) of 9.75M aqueous sodium hydroxide solution and an additional 1.2 ml. of triethylamine. Stirring was continued for 10 minutes, after which the phases were separated and the organic phase was washed with aqueous hydrochloric acid solution and three times with water. The solvent was vacuum stripped to yield a product containing cyclic bisphenol A polycarbonate oligomers in 85% yield, as determined by high pressure liquid chromatography.

In a control employing 200 mmol. of sodium hydroxide, the mixture gelled and analysis was impossible.

EXAMPLE 2

Following the procedure of Example 1, a bisphenol A bischloroformate solution in methylene chloride was titrated and was found to have a chloroformate concentration of 1.83M. It was converted to cyclic polycarbonate oligomers by a method similar to that of Example 1, using 274 mmol. of sodium hydroxide solution. The yield of bisphenol A cyclic polycarbonate oligomers was 88%. In a control reaction using 200 mmol. of base, the yield was 78%.

What is claimed is:

1. A method for determining the chloroformate concentration of a solution of at least one organic chloroformate in a substantially non-polar organic liquid which comprises the steps of combining said solution with at least one monohydroxyaromatic compound in stoichiometric excess with respect to chloroformate;

water, in the amount of about 5-25% by volume of said solution; and at least one 4-dialkylaminopyridine in the amount of about 1-10 mole percent based on the estimated amount of chloroformate; titrating said solution with aqueous base of known concentration under conditions facilitating reaction of chloroformate groups with the monohydroxyaromatic compound, and taking as the end point of the titration the volume of base which achieves complete conversion of chloroformate groups to monoaromatic carbonate groups as shown by a rapid rise in the pH of the aqueous phase of more than 2 points, to a value in the range of 7-11; and calculating the chloroformate concentration as one equivalent per equivalent of the base added.

2. A method according to claim 1 wherein the chloroformate is at least one bischloroformate derived from a dihydroxyaromatic compound of the formula HO—R—OH, wherein R is a divalent aromatic radical.

3. A method according to claim 2 wherein the monohydroxyaromatic compound is phenol.

4. A method according to claim 2 wherein the 4-dialkylaminopyridine is 4-dimethylaminopyridine.

5. A method according to claim 2 wherein R has the formula

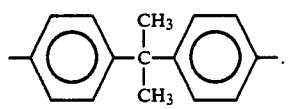

6. A method according to claim 2 wherein a portion of the R groups are 1,4-phenylene and the remainder have the formula

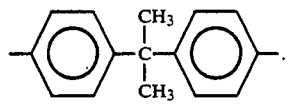

7. A method according to claim 2 wherein the non-polar organic liquid is methylene chloride.

8. A method according to claim 2 wherein the base is sodium hydroxide.

9. A method for preparing a cyclic polycarbonate composition which comprises the steps of determining the chloroformate concentration of a first portion of a solution of at least one aromatic bischloroformate in a substantially non-polar organic liquid by combining said solution with at least one monohydroxyaromatic compound in stoichiometric excess with respect to chloroformate; water, in the amount of about 5-25% by volume of said solution; and at least one 4-dialkylaminopyridine in the amount of about 1-10 mole percent based on the estimated amount of chloroformate; titrating said solution with aqueous base of known concentration under conditions facilitating reaction of chloroformate groups with the monohydroxyaromatic compound, and taking as the end point of the titration the volume of base which achieves complete conversion of chloroformate groups to monoaromatic carbonate groups as shown by a rapid rise in the pH of the aqueous phase of more than 2 points, to a value in the range of 7-11; and calculating the chloroformate concentration as one equivalent per equivalent of the base added and effecting conversion of a second portion of said bischloroformate to cyclic polycarbonate oligomers by condensation in the presence of a catalytic amount of at least one oleophilic aliphatic or alicyclic tertiary amine and about 3 moles of aqueous base per mole of bischloroformate.

10. A method according to claim 9 wherein the bischloroformate is derived from a dihydroxyaromatic compound of the formula HO—R—OH, wherein R is a divalent aromatic 11. A method according to claim 10 wherein the monohydroxyaromatic compound is phenol.

12. A method according to claim 10 wherein the 4-dialkylaminopyridine is 4-dimethylaminopyridine.

13. A method according to claim 10 wherein R has the formula

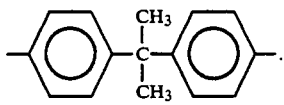

14. A method according to claim 10 wherein a portion of the R groups are 1,4-phenylene and the remainder have the formula

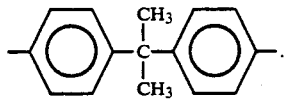

15. A method according to claim 10 wherein the non-polar organic liquid is methylene chloride.

16. A method according to claim 10 wherein the base is sodium hydroxide.

17. A method according to claim 10 wherein the tertiary amine is triethylamine.

* * * * *